United States Patent [19]

Alikhan

[11] Patent Number: 4,832,198
[45] Date of Patent: May 23, 1989

[54] CONTAINER FOR PACKAGING AND COUNTING SURGICAL SPONGES

[76] Inventor: Raza Alikhan, 55 Bamburgh Circle, Apartment 1407,, Scarborough, Ontario, Canada, M1W 3V4

[21] Appl. No.: 203,136

[22] Filed: Jun. 7, 1988

[30] Foreign Application Priority Data

Jun. 15, 1987 [CA] Canada .................................. 539682

[51] Int. Cl.⁴ ............................................. B65D 85/00
[52] U.S. Cl. .................................. 206/438; 206/509; 206/459; 206/362; 206/440
[58] Field of Search ................ 206/438, 362, 440, 459

[56] References Cited

U.S. PATENT DOCUMENTS

| | | | |
|---|---|---|---|
| 3,749,237 | 7/1973 | Dorton | 206/438 |
| 4,190,153 | 2/1980 | Olsen | 206/438 X |
| 4,234,086 | 11/1980 | Dorton | 206/362 |
| 4,361,231 | 11/1982 | Patience | 206/362 |
| 4,422,548 | 12/1983 | Cheesman et al. | 206/438 X |
| 4,429,789 | 2/1984 | Puckett, Jr. | 206/438 X |
| 4,494,653 | 1/1985 | Praderio | 206/438 X |

*Primary Examiner*—William Price
*Attorney, Agent, or Firm*—Ivor M. Hughes

[57] ABSTRACT

A single compartment container for packaging clean surgical sponges, each with an attached indicator tape, wherein the improvement uses the container, after the removal for the clean sponges, as a receptacle for holding, counting, confining and disposing discarded sponges with only the tapes inserted into specified locations in the container being counted, instead of the sponges, as indicative of their number.

3 Claims, 2 Drawing Sheets

CONTAINER FOR PACKAGING AND COUNTING SURGICAL SPONGES

BACKGROUND OF THE INVENTION

The invention relates to the packaging and counting of surgical sponges specifically made with an indicator attachment, usually in the form of a tape or string.

The most common sponge used in surgical procedures is a 4 ply absorbent cotton gauze pad in a number of sizes, stitched with a X-ray detectable material and a ½ inch wide tape formed into a 6 inch long loop. The tape is usually coloured blue for easier visibility when soaked in blood, and is securely sewn to anchor the sponge within a large body cavity by a surgical instrument. After usage, the nurses identify this type of sponge from other sponges used in surgery by its blue tape, especially while accounting for them to make sure that none have been inadvertently left within the body.

The tape sponge is usually packaged sterile in packs of five in a pouch. Alternately, it is placed with other products in a non-sterile condition inside various customized procedure packs made up by the hospital or commercial companies before being sterilized as a part of a larger whole unit. In either case, this invention serves to package, count and dispose tape sponges, though in the first instance it also functions as an independent sterile container in place of the plastic pouches generally in use.

All surgical procedures demand an accounting of the articles used in the field of surgery to prevent accidental misplacement within the body. None pose a greater problem than sponges. Operating room regulations therefore demand that they be counted at least three times by two nurses. The sponge is first discarded from the sterile field into a non-sterile bucket. A number of accessory products are then available for two nurses to count together from the bucket. The most common are ordinary plastic bags which are unsafe for this purpose, or an open plastic sheet on the floor which is very unhygienic.

The unsafe aspect of the use of a plastic bag for counting is primarily due to its inability to perform a second count on a batch of sponges, usually five, placed within one bag. If an error accidentally occurs while doing the single count into the bag, that error cannot be corrected by subsequent counts and can result in a serious miscount with harmful consequences. It therefore became necessary to devise more sophisticated products to count sponges, and these specialized sponge counting products are the commercial versions of Dorton's U.S. Pat. Nos. 3,749,237 and 4,234,086 and Cheesman/Alikhan's U.S. Pat No. 4,422,548. Regardless, all these patents teach methods of counting, but none of them or the articles commonly used provide an original package for clean sponges. Olsen's U.S. Pat. No. 4,190,153 describes a sponge tray comprising a separate section for clean sponges and several other compartments for physically separating each soiled sponge for counting.

As stated earlier, a requirement of good accounting policies is to be able to conveniently perform multiple counts of the sponges. To do so, the prior art devised various means to separately maintain each sponge in its own visually distinct compartment to enable the nurses to count them as desired. This invention, with only a single compartment, does not separate the bulk of the sponges for counting but uses the blue tape of each sponge as the sole visual indicator of each sponge and counts only the blue tapes inserted in a specified location, thereby permitting the use of the packaging container as a sponge counter. Since the count is done in the same containers from which the initial count of their original contents was made, the same number of sponges must be placed back into the same number of containers for a count to be correct and the sponges disposed, thereby eliminating the need of a separate product for counting or disposing.

Still further, a sponge counter should be able to confine a soiled and dirty sponge from contaminating the operating room environment by being exposed, while allowing it to be counted until the end of the operation. The present invention efficiently does this by completely enclosing the used sponges, while allowing the visible blue tapes in their locations to be counted any number of times.

Finally the containers may be conveniently stacked one on top of another in a small area. It saves valuable space in the operating room, and makes them easy to weigh on any scale or be viewed by a doctor to estimate blood loss. The containers do not have to be moved around to do a count as is the case with other commercial counters. Safety, sanitation, convenience and economy are the major considerations for a hospital in making a choice of the product to be used for counting sponges. This invention not only fulfils these important criteria of counting in a better manner through a high quality surgical package, but removes the expense and handling of another accessory to count and dispose used tape sponges.

SUMMARY OF THE INVENTION

This invention relates to a container for packaging clean surgical sponges, each attached to one indicator tape, after the removal of which, the same container is utilized to count and dispose used tape sponges. In particular, the taped sponges are confined in a single compartment to perform the multiple counts required during a surgical operation, with only the tapes inserted into specific locations being counted instead of the sponges as indicative of their number. Indeed, it is an important feature of this invention that the sponges may be repeatedly counted without being further handled, and completely confined without contamination of the operating room environment. The original packaging container is then used to safely dispose the sponges after the counts are done, eliminating the need of another product for these functions, while providing improved handling, ease of counting, convenience and economy. A more detailed explanation of the invention is provided in the following description and claims, and is illustrated in the accompanying drawings.

BRIEF DESCRIPTION OF THE DRAWINGS

These and other features and advantages of the present invention are more clearly described with the aid of the accompanying drawings, in which.

DESCRIPTION OF A SPECIFIC EMBODIMENT

It is to be noted that the drawings illustrate just one preferred embodiment of the invention. The container in general is designated 10 and the cover in general is designated 80 in all the figures.

Figure 1:
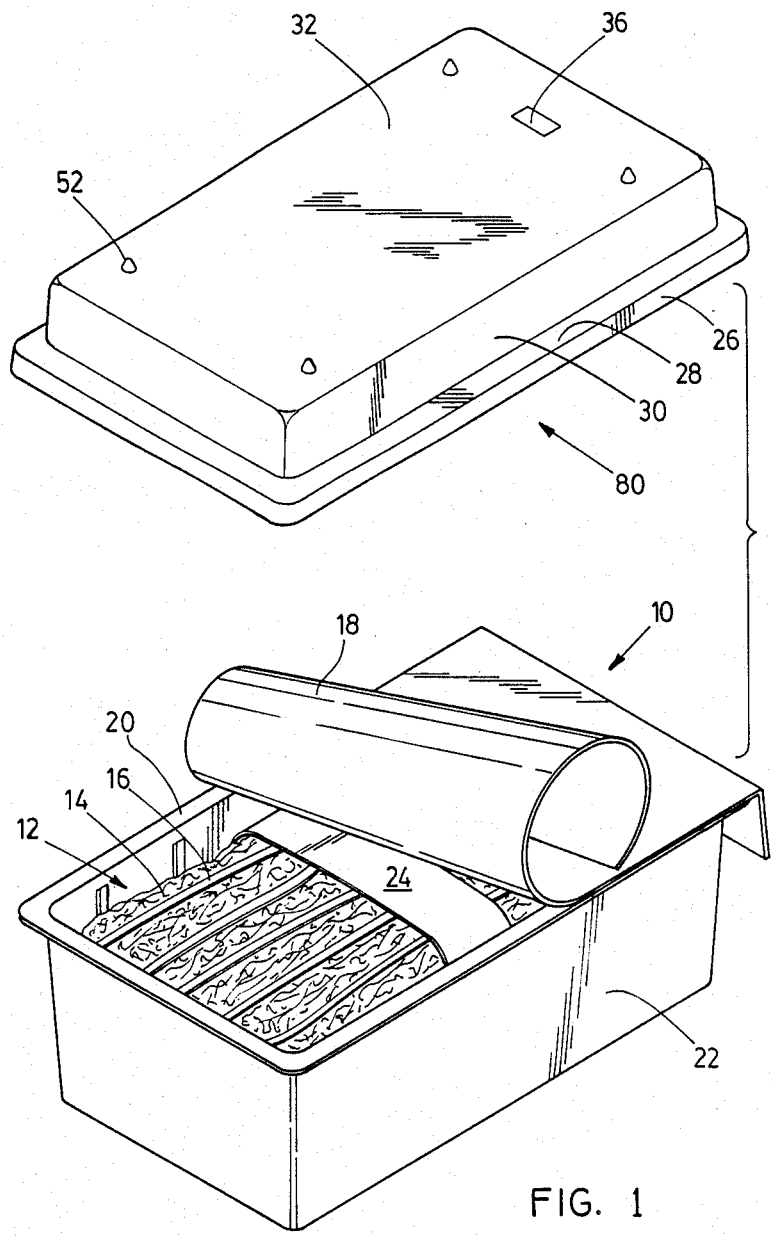
FIG. 1 is a general view of one embodiment of the container performing the function of a package containing clean surgical sponges, sterile seal and a separate cover.

FIG. 1 shows the sterile container 10 comprised mainly of a single compartment 12 packaged with five clean sponges 14, each having one indicator tape 16. The laminated film 18 has been partially peeled off from the flat sealing flange 20 of the container 10 and its wall 22. This film 18 will be completely peeled away before the sterile scrub nurse picks up the band 24 to remove the sterile sponges 14 from the sterile compartment 12. The outer perimeter of the cover 80 has a tapered edge 26 that forms a friction fit over flange 20 when closed. Within the perimeter edge 26 is a flat cover flange 28 that sits on the container flange 20 in the closed position, preventing any further compression by the cover 80 of the contents of the compartment 12. The rest of the cover 80 is raised upwards in the closed position by another tapered wall 30 to form a top surface 32 that accommodates the extra volume of used sponges in an unfolded condition. The cover 80 is non-sterile and should not touch the sterile portion or contents of the compartment 12 once the sterile seal formed by the film 18 is opened.

The empty weight of the container 10 and cover 80 is marked in the area 36 on the outer surface of the cover top 32. It enables the anesthesiologist to weigh the confined and therefore comparatively less dry sponges, in single or stacked containers, to obtain a more accurate estimate of blood loss during surgery. Alternatively, the transparent material of the container 10 and cover 80 permit a doctor to visually inspect the blood-soaked sponges confined in their containers to assess the blood loss.

Figure 2:
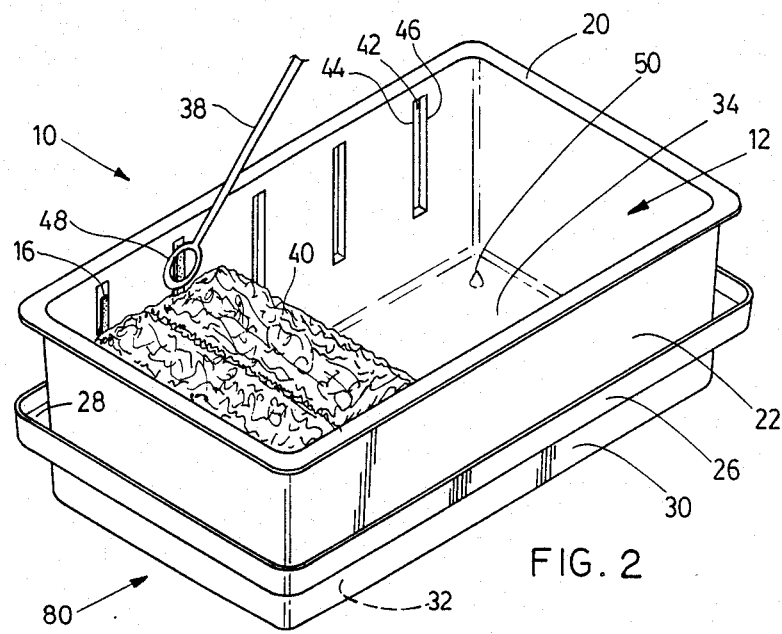
FIG. 2 shows the container functioning as a counter after the clean sponges are removed, with the indicator tapes of the soiled sponges being inserted into counting locations designed as grooves.

FIG. 2 is a drawing of the cover 80 positioned under the container 10 as a convenient way of keeping them together, without contacting sterile contents or surfaces, before covering the soiled sponges. The tapered cover wall 30 is designed to loosely fit around the container wall 22, which is also tapered downwards to the container floor 34. In this position, the floor 34 rests comfortably on the inside surface of the cover top 32, and the container wall 22 adjoins the inside of the cover wall 30. The container flange 20 and the cover flange 28 and perimeter edge 26 extend out for easy separation of container and cover.

The non-sterile circulating nurse, usually using a gloved hand (not shown) and a sponge stick 38, picks up one soiled sponge 40 by its attached indicator tape 16 from the bucket. She places the soiled sponge 40 on the floor 34 and inserts its indicator tape 16 into a groove 42 formed along one length of the container wall 22. The groove 42 runs vertically upwards along the wall 22, stopping a fraction of an inch below the flange 20, so as not to interfere with the sealing of this flange by the laminating film 18. The groove 42 is itself formed as an outward protrusion of container wall 22 by two sides 44 and 46 extending the single compartment 12 outwards. The width of the groove 42 along the wall 22 is about the width of the sponge stick clamp 48 ($\frac{1}{2}$ inch) and the width of the sides 44 and 46 are about the same size.

Once the nurse has inserted the indicator tape 16 into the groove 42, the main bulk of the soiled sponge 40 forms the fourth wall of the groove 42 to hold the indicator tape 16 in its inserted visible position in groove 42. The closing of the container 10 by the cover 80 confines the discarded sponges 40 within the compartment 12 to prevent contamination of the operating room environment. The situation of the grooves 42 along one length of the container wall 22 is such that each groove is located in the middle of five approximately equal divisions of the wall length, so that five equally spaced, visually clear, serially numbered and well differentiated specific segments are seen from the outside of the container for counting. The tub floor 34 has four small protrusions 50 located near its four corners for stacking containers, one on top of the other.

Figure 3:
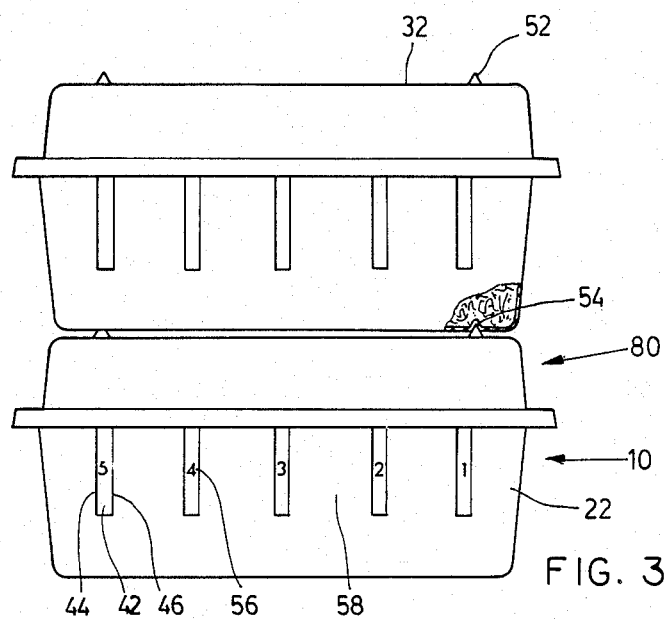
FIG. 3 illustrates the closed and stacked containers with the indicator tapes of the confined sponges visible from the outside in their grooved locations for counting.

These last few features are better seen in FIG. 3 with the container 10 being covered by the cover 80. The protrusions of the tub floor mentioned above fit the protrusions 52 formed in the cover top surface 32 to allow the containers to be stacked, and this arrangement is shown as 54. The five counting locations in the wall 22 are serially numbered from the outside with a number 56 from one to five. The inserted indicator tape 16 of each sponge, blue in colour, will be clearly distinguished behind the number 56 against a white or blood-soaked red sponge. It may be more desirable to mottle the areas 58 between the grooves 42 along this one length of the wall 22 so that the transparent grooves are more differentiated for counting the indicator tape 16. It can be done by simply texturing the inner surface of the mold. Once all the counts, blood loss estimates and other procedural requirements are over, the containers are disposed, their contents safely counted and contained in the original package in which they were initially delivered for use in the surgical procedure.

The main part of the container is a single compartment 12, vacuum formed in its preferred embodiment from a transparent, semi-rigid, thermoplastic material on a packaging machine, to hold clean surgical sponges. When a sterile package is required, the compartment 12 is sealed around the container flange 20 by the same machine with a layer of coated paper or laminated film 18, which is peeled off completely for the removal of its contents. Various surgical products are presently available in such a package. After removal of the clean sponges, the improvement to the container utilizes the same compartment as a receptacle to hold discarded sponges for counting their attached indicator tapes 16 inserted in special locations 42.

In its preferred embodiment, a covering lid 80 is separately vacuum formed from a similar material as the container. However the container and cover may be formed together with a hinge instead of being separate. The container may also be used without any cover at all. It will still hold, count and dispose the taped sponges. When present as a separate or hinged part, the perimeter edge 26 of the cover has the same configuration as the container flange 20 and is slightly larger to become a friction fit enclosure on closing. While functioning as a sterile package, the cover protects the film for sterile contents from dust and damage. After removal of the original contents, it confines and contains the counted sponges, while allowing the containers to be neatly stacked and safely disposed.

The single compartment 12 is shaped to hold the desired number of sponges without any divisions. The cover is similarly without divisions. However, there are a similar number of tape insertion locations as sponges packaged. These location means may be situated in either the container or the cover or the hinge, if the two are connected, and may be formed as grooves, hooks or retaining slots. In the preferred embodiment, the location means are shown as grooves along one length of the container wall. However, an automated process for die cutting the container on a packaging machine would lend itself well for locating die cut slots that retain the indicator tapes 16 along one extended edge of the container flange length or in the hinge, but away from the sealing surface flange area 20 shown in the figures.

The technique of inserting the tape for counting is specially convenient for the nurse as it is the present practice to pick a sponge by its tape for identifying and separating, prior to counting. It is therefore particularly important that the location design for inserting the tape with a sponge stick or gloved hand, and release the tape in a visible position, permits this action to be done easily by the circulating nurse.

The method of counting in the operating room is for the circulating nurse to pick up one discarded sponge from the bucket by its tape, show it to the scrub nurse and place it in the container, inserting the counted tape into one location in a sequential manner as a single count. Because of the clarity of the material of the container and cover, the inserted tapes in their respective locations are plainly visible from the outside for verifying the count, even after the cover is closed.

From this description it can be seen that an excellent surgical package is turned into a counter by the tape location means. Once each sponge is separately counted and their corresponding tape inserted into one viewing location, the cover is placed into position to form a completely enclosed container that confines, contains and disposes soiled sponges, while showing their tapes for repeated counts to be made during the entire surgical procedure. The closed containers may be neatly stacked and without being moved, will continue to show the tapes for counting at any time. As the closed cover is simple to open, the enclosed sponges may be removed from the container for a total recount, if required due to an error detected in tallying the count.

The foregoing is a description of a preferred embodiment of the invention which is given here by way of an example only. The invention is not to be taken as limited to any of the specific features described, but comprehends all such variations thereof as come within the scope of the appended claims.

What is claimed is:

1. A single compartment container for packaging clean surgical sponges, each with one attached indicator tape, after the removal of which said clean sponges, the container is used as a receptacle to hold, count and dispose the same number of discarded sponges with said attached indicator tapes as said clean sponges originally packaged, wherein the improvement comprises:
   location means to insert one said attached indicator tape of each said discarded sponge;
   the location means being the same in number as said clean sponges originally packaged;
   said number of the location means being distinctly separated from each other for counting the inserted said attached indicator tapes of said discarded sponges.

2. A single compartment container for packaging clean surgical sponges, each with one attached indicator tape, after the removal of which said clean sponges, the container is used as a receptacle to hold, count, confine and dispose the same number of discarded sponges with said attached indicator tapes as said clean sponges originally packaged, wherein the improvement comprises;
   A cover of approximately the same shape and size as the outer perimeter of the container to form an enclosure for confining said discarded sponges; the cover being a separate part to the container;
   and location means in the container to insert one said attached indicator tape of each said discarded sponge;
   the location means being the same in number as said clean sponges originally packaged;
   said number of the location means being distinctly separated from each other for counting the inserted said attached indicator tapes of said discarded sponges.

3. A container as claimed in claim 1 or 2 with a sealing means to maintain the sterility of the single compartment and said clean sponges until opened or damaged.

* * * * *